United States Patent [19]

Findlay et al.

[11] Patent Number: 4,703,002

[45] Date of Patent: Oct. 27, 1987

[54] METHOD FOR PREPARING COATING COMPOSITIONS CONTAINING AN IMMUNOLOGICALLY REACTIVE SPECIES AND ELEMENTS CONTAINING SAME

[75] Inventors: John B. Findlay, Rochester; Annie L. Wu, Penfield, both of N.Y.

[73] Assignee: Eastman Kodak Company, Rochester, N.Y.

[21] Appl. No.: 729,332

[22] Filed: May 1, 1985

[51] Int. Cl.$^4$ ............... G01N 33/543; G01N 33/545; G01N 33/548; G01N 33/549
[52] U.S. Cl. ........................... 435/17; 422/56; 422/57; 435/805; 436/518; 436/530; 436/531; 436/535; 436/810; 427/2
[58] Field of Search ............... 436/518, 528, 530, 531, 436/810, 169, 170, 523, 527, 529, 535; 435/805, 17; 422/56, 57; 427/2

[56] References Cited

U.S. PATENT DOCUMENTS

| 3,992,158 | 11/1976 | Przybylowicz et al. | 23/253 |
| 4,052,010 | 10/1977 | Baker et al. | 241/20 |
| 4,067,775 | 1/1978 | Wurzburg et al. | 435/17 |
| 4,200,690 | 4/1980 | Root et al. | 436/531 |
| 4,237,044 | 12/1980 | Wurzburg et al. | 436/811 |
| 4,310,513 | 1/1982 | Fauve | 424/80 |

FOREIGN PATENT DOCUMENTS 116307  1/1984  European Pat. Off. .

Primary Examiner—Sidney Marantz
Assistant Examiner—David A. Saunders
Attorney, Agent, or Firm—J. Lanny Tucker

[57] ABSTRACT

A method for preparing a blush polymer coating composition containing an immunologically reative species comprises milling the species and the other materials used in the composition to uniformly disperse the species therein. This coating composition can be used to prepare analytical elements for determining analytes (e.g. creating kinase-MB) whereby the effects of potential interferents are immunochemically removed. By milling the immunologically reactive species, e.g. antisera, into the coating composition, the resulting element has improved stability resulting in improved keeping in high humidity environments.

20 Claims, 3 Drawing Figures

METHOD FOR PREPARING COATING COMPOSITIONS CONTAINING AN IMMUNOLOGICALLY REACTIVE SPECIES AND ELEMENTS CONTAINING SAME

FIELD OF THE INVENTION

The present invention relates to clinical chemistry. In particular, it relates to a method for preparing blush polymer coating compositions which contain an immunologically reactive species. It also relates to a method of making analytical elements containing the coating composition. Further, this invention relates to elements particularly useful for assays of analytes in aqueous liquids, e.g. biological fluids.

BACKGROUND OF THE INVENTION

Often in the analysis of aqueous fluids for chemical or biological substances (herein called analytes), the results of the analysis can be adversely affected by interfering materials. These materials either interfere with the reactivity of the analyte or act so similarly to it that the properties of analyte and interferent cannot be distinguished. For example, in the determination of certain isoenzymes, it is often necessary to minimize or eliminate the effect of the isoenzymes which are not of interest.

Creatine kinase (abbreviated herein to CK, but also known as creatine phosphokinase, CPK, or ATP: creatine phosphotransferase E.C.2.7.3.2.) occurs in human body fluids and tissue in the form of three isoenzymes: CK-MM, for example in muscles, CK-BB, for example in the brain, and CK-MB, for example in the myocardium. The CK activity occurring in healthy human blood serum is normally due to the CK-MM isoenzyme because CK-BB does not generally pass into the blood stream. In a healthy individual, CK-MB is generally restricted to certain organs, for example the myocardium. However, when the myocardium is damaged, as in the case of a cardiac infarction, CK-MB is released into the blood stream and can be detected therein.

A potential difficulty encountered in methods for determining CK-MB in biological fluids is interference from the other two isoenzymes. For practical purposes, the amount of CK-BB in the fluid is considered negligible in most determinations. In methods for determining CK-MB, it is known to precipitate or inhibit the M subunit with specific antibodies to eliminate the interference of CK-MM on the assay and then to measure the remaining isoenzyme CK-MB.

A relatively recent contribution to clinical chemistry was the development of dry multilayer analytical elements useful for the assay of liquids. Such elements are described, for example, in U.S. Pat. No. 3,992,158 (issued Nov. 16, 1976 to Przybylowicz et al). These elements generally have an outer spreading layer which is known as a porous "blush" polymer layer (see Col. 7, lines 44–64) composed of a polymeric binder and a particulate material which increases layer porosity.

A number of analytical elements having such spreading layers have been designed for various assays and used commercially, including an element useful for the determination of total CK. In the preparation of such elements, it has been standard practice to incorporate some reagents into the spreading layer by means of a wash coat. In other words, the spreading layer is coated and dried, and an aqueous suspension of the reagent(s) is applied to it and allowed to soak into the spreading layer. The aqueous medium carries the reagent(s) throughout the spreading layer.

It has been attempted to incorporate antibodies for CK-MM into a spreading layer in this manner (i.e. as a wash coat). However, it has been observed that the resulting element has reduced stability in high humidity environments, i.e. at least about 50% relative humidity at 25° C. Moreover, manufacturing processes used in making analytical elements are necessarily carried out in this type of environment. The reduced stability under such conditions is a serious problem. It limits the flexibility in handling the elements by both the manufacturer and the user. The manufacturer must try to limit the amount of time the element is subject to high humidity. Further, if a user accidentally leaves the element out of the freezer compartment it is normally kept in prior to use, the element is likely to give erroneous results in the assay.

It would be desirable to improve the stability, and hence the room temperature keeping properties, of analytical elements containing active antisera which have blush polymer spreading layers like those described in the Przybylowicz et al reference noted above.

SUMMARY OF THE INVENTION

We have discovered a means for improving the stability of the elements described above and of overcoming the problems associated with known manufacturing methods. More specifically, we have found that a dehydrated immunologically reactive species can be uniformly milled into a blush polymer spreading layer composition prior to coating and subsequently coated to provide a highly stable element under high humidity conditions. It was also surprising to us that the species remained active after milling in organic solvents because of the high shear and potentially deactivating environment of the process. The resulting element has improved room temperature (25° C.) keeping properties under the high humidity conditions (i.e. 50% relative humidity) generally encountered in manufacturing as well as during the ultimate use. In particular, the element exhibits at least about 75% retained sensitivity after being kept at 25° C. and 50% relative humidity for 6 days.

Therefore, in accordance with this invention, a method for preparing a blush polymer coating composition containing an active immunologically reactive species comprises milling a dehydrated immunologically reactive species a particulate material and a polymeric binder material in an organic solvent for a time sufficient to uniformly disperse the species as particles less than about 5 μm in diameter in the binder material.

This invention also provides a method for preparing an analytical element comprising a porous blush polymer layer containing an active immunologically reactive species. This method comprises applying the coating composition described above to a support.

Further, this invention provides an analytical element comprising a support having thereon a porous blush polymer spreading layer containing an active immunologically reactive species. This element exhibits at least about 75% retained sensitivity after being kept at 25° C. and 50% relative humidity for at least 6 days.

BRIEF DESCRIPTION OF THE INVENTION

DETAILED DESCRIPTION OF THE INVENTION

Figure 2:
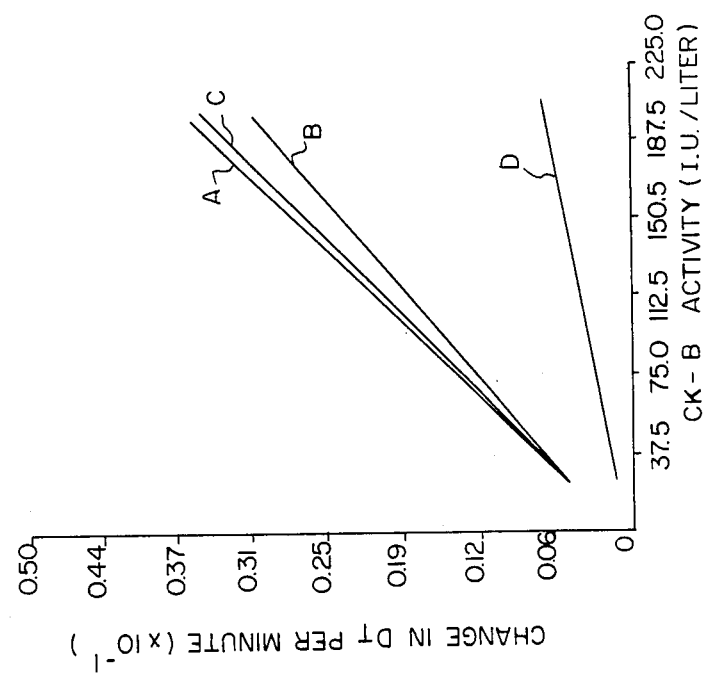
FIG. 2 is a graphical illustration of rate of change in transmission density ($D_T$) vs. CK-B activity for a number of compared elements as discussed in Example 3 below.

The present invention relates to the preparation of blush polymer coating compositions and the elements containing same which can be used to determine any of a number of analytes where it is desirable to have an active immunologically reactive species (e.g. antisera) in the element, preferably in a spreading layer. In particular, the resulting elements can be used to assay biological fluids of either humans or animals, but preferably of humans. Such fluids include, but are not limited to, whole blood, plasma, sera, lymph, bile, urine, spinal fluid, sputum, perspiration and the like as well as stool secretions. The elements can also be used to assay fluid preparations of human or animal tissue such as skeletal muscle, heart, kidney, lungs, brains, bone marrow, skin and the like.

The elements of the present invention contain an active species which participates in an immunochemical reaction with a potentially interfering material in the fluid being assayed. The term "immunologically reactive species" is meant to include any compound which will complex with a chemical or biological interferent and thereby limit its effect on the assay. In general, such species include antibodies for a protein (e.g. and enzyme) found in antisera or small molecule (e.g. a therapeutic drug). Alternatively, if the potential interferent is an antibody, the species can be an anti-antibody, that is, a second antibody designed to complex with the first antibody.

More particularly, the immunologically reactive species is an antibody for an isoenzyme where that isoenzyme is a potential interferent for the determination of another isoenzyme. For example, the element can be used to determine an isoenzyme of lactate dehydrogenase (LDH) with antisera containing antibodies for the undesired LDH isoenzymes. A solution LDH-1 assay using immunochemical techniques is described in U.S. Pat. No. 4,224,406 (issued Sept. 23, 1980 to Gomez et al)

Although the present invention is not so limited, the remainder of the detailed description will be directed primarily to the preparation of spreading layer compositions and elements useful for CK-MB determinations.

The elements of this invention can be used in an immunochemical method for selectively determining CK-BB, CK-MM or CK-MB in a biological fluid which also possibly contains one or more of the isoenzymes. The CK-MM isoenzyme is a potentially significant interferent when CK-MB is to be measured. By removing the effect of this interferent, the detectable change produced in the assay can then be directly correlated to the amount of CK-MB in the fluid sample. The details of an assay, analytical element and the reagents needed for CK-MB determination are provided in copending and commonly owned U.S. Ser. No. 729,333, of Findlay and Wu, entitled IMMUNOCHEMICAL METHOD AND ANALYTICAL COMPOSITION AND ELEMENT FOR DETERMINATION OF CREATINE KINASE-MB, and U.S. Ser. No. 729,331 of Findlay, Wu and Norton, entitled ANALYTICAL ELEMENT AND METHOD FOR DETERMINATION OF TOTAL CREATINE KINASE OR AN ISOENZYME, both filed on even date herewith, the disclosures of which are incorporated herein by reference.

The coating composition of this invention is prepared by milling a dehydrated immunologically reactive species, such as antisera containing antibodies, one or more particulate materials and one or more polymeric binders in one or more organic solvents.

Antibodies useful n the practice of this invention which are specific to the interferent of concern, e.g. CK-MM, can be generated from antisera using known procedures. The antibodies can be isolated from the antisera before use, or unpurified antisera can be used. Antisera is generally obtained from suitably innoculated monkeys, pigs, horses, goats, rabbits, rats, mice, chickens, cattle, or other animals known to be useful for this purpose. A preferred source of antibodies are suitably innoculated goats. The antibodies are generally used in a substantially dried form (i.e. dehydrated form). The antisera can be dried using any suitable technique known to one skilled in the art. Generally, the antisera is lyophilized. Lyophilization is accomplished using known procedures, such as by conventional freeze drying processes. Further details of useful antibodies for CK-MM are provided, for example, in U.S. Pat. Nos. 4,237,044 (issued Dec. 2, 1980 to Wurzburg et al) and 4,260,678 (issued Apr. 7, 1981 to Lepp et al), the disclosure of which are incorporated herein by reference.

Polymeric binders useful in preparing the coating composition of this invention include any polymers which can be made into a "blush" polymer layer. Such layers can be formed on a supporting material by dissolving a polymer in a mixture of two organic liquids, one of which is a lower boiling, good solvent for the polymer and the other being a higher boiling non-solvent or poor solvent for the polymer. Such a polymer solution is then coated on the supporting material, and dried under controlled conditions. The lower boiling solvent evaporates more readily and the coating can become enriched in the liquid which is a poor solvent or non-solvent. As evaporation proceeds under proper conditions, the polymer forms an isotropically porous layer. Many different polymers can be used, singly or in combination, for preparing isotropically porous blush polymer layers, examples being polycarbonates, polyamides, polyurethanes and cellulose esters. Cellulose acetate is a preferred polymer.

The void volume of the resulting spreading layer is desirably at least about 25 percent. As can be appreciated, void volume can be controlled, for example, by selecting particulate materials of appropriate size, or by varying the solvents or drying conditions of the coating. It is preferred that the porosity be provided by including one or more particulate materials in the composition. Such materials are generally inorganic materials, such as inorganic pigments, which are chemically inert to sample components under assay. Pigments such as titanium dioxide, barium sulfate, zinc oxide, lead oxide, etc. are desirable, with titanium dioxide being most preferred. Other useful particulate materials include diatomaceous earth and microcrystalline colloidal materials derived from natural or synthetic polymers. Microcystalline cellulose, which is commercially available as Avicel ™ from FMC Corporation (Chicago, Ill.) is a useful colloidal material. Resinous or glass beads, are also useful. The particle size of the particles is not critical and can be chosen to give a desired porosity.

The blush polymer coating composition materials are generally prepared in an organic solvent according to known procedures described, for example, in U.S. Pat. No. 3,992,158, noted above. Useful solvents vary depending upon the polymeric binders chosen. For cellulose acetate, for example, useful solvents include acetone, dichloroethane o-xylene and m-xylene, or a mixture of two or more of them. Other useful solvents for various binder materials include alcohols and the like. It was surprising that the immunologically reactive species remained active after being milled in the organic solvent environment.

Other addenda commonly added to blush polymer spreading layer compositions can be included in the composition of this invention, including surfactants, buffers, resins, refractive pigments, etc. Some spreading layers contain reagents used in the assay. For example, in CK-MB elements, the composition preferably includes an activator for CK e.g. N-acetylcysteine.

The materials of the coating composition are present in amounts known to one skilled in the art. While the coated amount of immunologically reactive species will vary depending upon the effectiveness of the species used, generally it is present in an amount of at least about 5000 U/m$^2$ of dry coating coverage. For example, the dry coverage of immunologically reactive species is preferably from about 15,000 to about 30,000 U/m$^2$. As used herein, the level of immunologically reactive species is given in Units (U) which are defined by the titer assay: (50% inhibition titer) (m$\lambda$/0.093 m$^2$)=U/m$^2$. The particulate material is generally present in an amount which provides at least about 20, and preferably from about 40 to about 60, g/m$^2$ of dry coverage. The binder material is generally present in an amount to provide at least about 2, and preferably from about 5 to about 8, g/m$^2$ of dry coverage. The suitable amount of organic solvent used to prepare the compositions can be readily determined by a worker skilld in the art.

The materials described above are milled together to form a uniform dispersion. Several milling techniques are useful, e.g. ball milling, pebble milling and sand milling. The amounts of materials, type of equipment and length of milling time are dependent on desired particle size, and can be determined by one skilled in the art. The time of milling is not critical as long as the antisera is uniformly dispersed within the polymeric binder material in acceptably small particle sizes, e.g. less than about 5 $\mu$m in diameter, and preferably less than about 3 $\mu$m in diameter. The other components of the composition are also uniformly dispersed in the polymeric binder with the milling. Despite the high shear in the milling process, the immunologically reactive species, e.g. antibodies, generally retains sufficient activity to reduce the activity of about 2,500 I.U./$\lambda$ of CK-MM isoenzyme in human sera to less than about 5 I.U./$\lambda$.

Once the coating composition is sufficiently milled, it is coated on a suitable supporting material using conventional coating techniques and equipment. The drying conditions are controlled as described above to "blush" the resulting layer and to provide the desired porosity. The resulting porous spreading layer is carried on a nonporous, supporting material (commonly called a support). Such a support can be any suitable dimensionally stable, and preferably transparent (i.e. radiation transmissive) material which transmits electromagnetic radiation of a wavelength between about 200 and 900 nm. A support of choice for a particular element should compatible with the intended mode of detection (fluorescence or colorimetric spectroscopy). Useful supports can be made from paper, metal foils, polytyrene, polyesters [e.g. poly(ethylene terephthalate)], polycarbonates, cellulose esters (e.g. cellulose acetate), etc.

The blush polymer spreading layer can be the sole layer in the element on the support. Alternatively, it can be one of two or more layers and be immediately adjacent to the support. Preferably it is the outermost layer of a multilayer element which has one or more intermediate layers between it and the support. Any of a number of intermediate layers can be incorporated in the element for various purposes as is known in the art, including particulate (e.g. beaded) or fibrous spreading layers which are not blush polymer layers, radiation-blocking layers, reagent layers, registration layers, subbing layers, filtering layers, barrier layers, etc. The composition of such layers is known to one skilled in the art as described in the Przybylowicz et al reference noted above as well as in U.S. Pat. Nos. 4,042,335 (issued Aug. 16, 1977 to Clément), 4,132,528 (issued Jan. 2, 1979 to Eikenberry et al), 4,144,306 (issued Mar. 13, 1979 to Figueras), 4,292,272 (issued Sept. 29, 1981 to Kitajima et al), 4,430,436 (issued Feb. 7, 1984 to Koyama et al), and 4,258,001 (issued Mar. 24, 1981 to Pierce et al).

In a preferred embodiment of this invention, an element is prepared having a support having thereon, in order and in fluid contact, a registration layer, a reagent layer and a spreading layer prepared from the blush polymer composition described above.

This element is advantageously used to determine CK-MB and has a substrate for the enzyme, e.g. creatine phosphate, in the reagent layer and the appropriate reagents and indicator composition in one or more of the other layers. The details of such an element are provided in either of U.S. Ser. Nos. 729,331 or 729,333, noted above.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, analyte (e.g. CK isoenzyme) determination is made by taking the element from a supply roll, chip packet or other source and physically contacting it with a sample (e.g. 1-100 $\mu$l) of the liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

The analyte (e.g. CK isoenzyme) added to the element in the test sample then catalyzes reaction of the reagents (e.g. ADP with the creatine phosphate substrate) at a rate based on the amount of analyte present in the sample. The rate of detectable change (e.g. dye formation) due to the reaction (e.g. of creatine phosphate) or formation of the reaction product (e.g. ATP) is determinable by passing the element through a zone in which suitable detection apparatus for reflection or transmission spectrophotometry, potentiometry or photometry, is provided. Suitable detection apparatus and procedures are known in the art.

In the examples which follow, illustrating the practice of the present invention, the materials used were obtained as follows: Estane TM 5715 polyurethane resin from B. F. Goodrich (Cleveland, Ohio), Triton TM X-200E and X-405 from Rohm and Haas (Philadelphia, Pa.), magnesium acetate from Allied Chemical Corp. (Morristown, N.J.), glycerol kinase from Worthington (Freehold, N.J.), adenosine-5'-monophosphate (AMP), adenosine-5'-diphosphate (ADP) and $P_1,P_5$-di(adenosine-5')pentaphosphate (DAPP) from Sigma Chemical Co. (St Louis, Mo.), creatine phosphate from Calbiochem (San Diego, Calif.), Alkanol XC TM from DuPont (Wilmington, Del.), peroxidase from Miles Laboratories (Elkhart, Ind.), α-glycerophosphate oxidase from Toyo Jozo (shizuoka, Japan), and the remainder either from Eastman Kodak Company (Rochester, N.Y.) or prepared using conventional procedures and starting materials.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

Also, as used herein, percent sensitivity retained (% sens. ret.) is defined as:

$$[(Rate_2 - Rate_1) \text{ at high humidity} \div (Rate_2 - Rate_1) \text{ at low humidity}] \times 100$$

wherein $Rate_2$ is the analyte activity determined using a test fluid containing a relatively high level of analyte, and $Rate_1$ is the analyte activity determined using a test fluid containing a relatively low level of analyte.

High humidity is at least about 50% relative humidity (at 25° C.), and low humidity is at most 15% relative humidity (at −18° C.). The % sens. ret. is determined after the elements have been kept under defined conditions for a period of time, e.g. 6 or 7 days.

EXAMPLE 1

Preparation of a Blush Polymer Coating Composition

A blush polymer coating composition was prepared in the following manner. This coating composition was useful in the preparation of an analytical element designed for the assay of CK-MB.

Antisera containing goat anti-human CK-MM was obtained by immunizing goats with purified human CK-MM and withdrawing serum or plasma. The antisera was purified using known techniques in the art. The antisera was lyophilized to a dry powder by a conventional freeze drying process.

The following dispersion was ball milled for at least 8 hours using conventional ball milling techniques: lyophilized antisera described above (200–500 mλ), ethylenebis(oxyethylenenitrilo)-tetraacetic acid (6–10 g), titanium dioxide (800 g), cellulose acetate (110 g) and Triton TM x-405 surfactant (26 g) in 1:1 acetone/m-xylene. After ball milling, 4–7 g of N-acetylcysteine CK activator was then mixed into the dispersion. The resulting coating composition contained the active antisera uniformly distributed within the polymeric binder material as particles having a diameter of less than about 5 μm.

EXAMPLE 2

Preparation and Use of an Analytical Element for Determination of CK-BB

An analytical element having the format and components illustrated below was prepared using conventional coating techniques except for introducing antisera into the spreading layer. The spreading layer was formed by coating a ball milled coating composition prepared like that in Example 1 onto the underlying layers and drying it under controlled conditions to form a blush polymer layer.

| | | |
|---|---|---|
| Spreading Layer | Goat anti-human CK-MM | 5,000–300,000 U/m² |
| | Titanium dioxide | 20–80 g/m² |
| | Cellulose acetate | 2–10 g/m² |
| | N—acetyl-L-cysteine | 0.2–0.6 g/m² |
| | Ethylenebis(oxyethylenenitrilo)tetraacetic acid | 0.2–0.8 g/m² |
| | Triton TM X-405 | 0.5–3 g/m² |
| Subbing Layer | Poly(N—isopropylacrylamide) | 0.2–0.6 g/m² |
| Reagent Layer | Gelatin (hardened) | 2–8 g/m² |
| | Magnesium acetate | 0.2–2 g/m² |
| | Triton TM X-200E surfactant | 0.005–0.5 g/m² |
| | Glycerol kinase | 2,000–10,000 I.U./m² |
| | Adenosine-5'-diphosphate (ADP) | 0.04–0.2 g/m² |
| | Adenosine-5'-monophosphate (AMP) | 0.2–2 g/m² |
| | $P_1,P_5$-di(adenosine-5')-pentaphosphate (DAPP) | 0.01–0.1 g/m² |
| | Glycerol | 0.1–0.3 g/m² |
| | Creatine phosphate | 1–4 g/m² |
| | 2-[Bis(2-hydroxyethyl)imino]-2-(hydroxymethyl)-1,3-propanediol buffer | 1–5 g/m² |
| Registration Layer | Gelatin (hardened) | 5–15 g/m² |
| | 2-[Bis(2-hydroxyethyl)imino]-2-(hydroxymethyl)-1,3-propanediol buffer | 1–5 g/m² |
| | Alkanol XC TM surfactant | 0.1–0.5 g/m² |
| | 2-(3,5-Dimethoxy-4-hydroxyphenyl)-4,5-bis(4-dimethylaminophenyl)imidazole | 0.1–0.3 g/m² |
| | Glycolic acid | 0.1–0.5 g/m² |
| | 5,5-Dimethyl-1,3-cyclohexanedione | 0.01–5 g/m² |
| | Triton TM X-200E surfactant | 0.05–1 g/m² |
| | 2,4-Di--pentylphenol | 1–3 g/m² |
| | Peroxidase | 10,000–50,000 I.U./m² |
| | Ascorbic acid oxidase | 6,000–12,000 g/m² |
| | L-α-Glycerophosphate oxidase | 1,000–10,000 g/m² |
| | Poly(ethylene terephthalate) Support | |

Similar analytical elements were prepared by wash coating the antisera into an already coated and dried blush polymer spreading layer having the same composition except for the antisera. No milling was used to prepare the Control spreading layer. These elements are labeled Control elements in this example.

Figure 1:
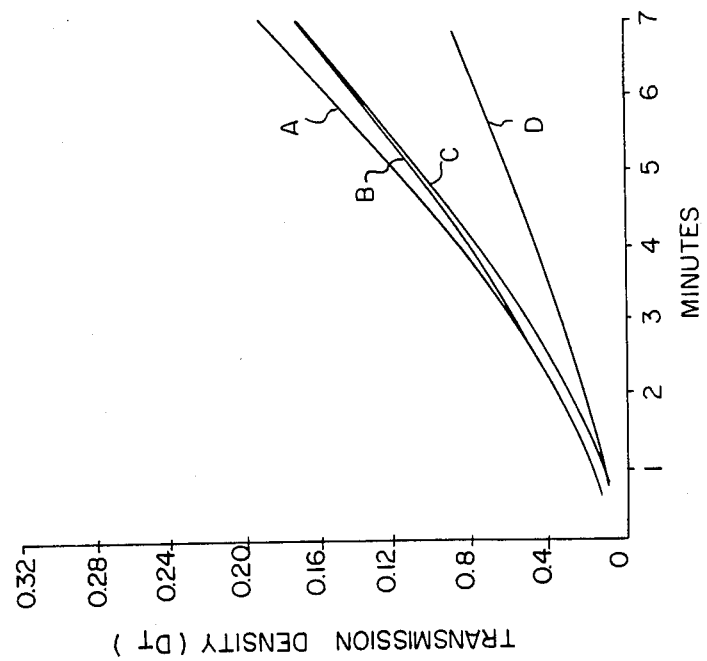
FIG. 1 is a graphical illustration of transmission density ($D_T$) vs. time for the determination of CK-BB using elements prepared according to this invention compared to elements prepared by known techniques and demonstrating the improved stability obtained with this invention as discussed in Example 2 below.

Both types of elements were tested for stability or keeping properties. Both elements were kept for 7 days under two different keeping conditions: 25° C. and 50% relative humidity, and −18° C. and 15% relative humidity. The elements were then used to determine the CK-BB isoenzyme activity in a test sample of fluid containing 247 I.U./λ CK-BB. The resulting dye formation in the elements was determined using a modified conventional spectrophotometer at 37° C. and 670 nm over seven minutes. FIG. 1 shows the results of these tests. Curves A–D of FIG. 1 are identified in Table I below.

TABLE I

| Curve - Element | Keeping Conditions |
| --- | --- |
| A - Example 2 | −18° C., 15% relative humidity |
| B - Example 2 | 25° C., 50% relative humidity |
| C - Control | −18° C., 15% relative humidity |
| D - Control | 25° C., 50% relative humidity |

The data show that the element prepared according to the present invention has significantly improved stability and keeping properties over the Control element. This improvement is seen by comparing the small difference between curves A and B versus the larger difference between curves C and D. The difference between the two curves of each set of curves represents the loss in stability due to keeping under high humidity conditions (curves B and D). The greater the difference between the curves of each set, the greater the instability of the element. The element prepared according to this invention whereby the antisera was ball milled into the spreading layer composition demonstrated significant stability improvement in high humidity environments. The Control element exhibited considerable stability loss. The element of the invention exhibited greater than about 75% sens. ret. whereas the Control element exhibited less than about 50% sens. ret.

EXAMPLE 3

Preparation and Use of a Different Analytical Element Embodiment for Determination of CK-BB An analytical element was prepared similarly to that illustrated in Example 2 using conventional coating techniques. The spreading layer of the element was prepared by coating the ball milled coating composition of Example 1 onto the underlying layers and forming a blush polymer layer.

This element was different from that of Example 2 in the placement of some reagents. In particular, the reagent layer contained ascorbic acid oxidase while the registration layer contained creatine phosphate, adenosine-5′-diphosphate, glycerol and glycerol kinase. Magnesium acetate was placed in both the reagent and registration layers.

Similar elements were prepared by wash coating the antisera into an already coated and dried blush polymer spreading layer having the same composition except for the antisera. No ball milling was used to prepare the Control spreading layer. These elements are labeled Controls in this example.

Each type of element was kept under the conditions described in Example 2 and tested for stability or keeping properties by spotting them with test fluids having known amounts of CK-BB isoenzyme. The rate of enzyme activity was measured between 6 and 7 minutes after incubation at 37° C. using a modified conventional spectrophotometer at 670 nm. FIG. 2 shows the results for each element. Table II below indicates the keeping conditions for the illustrated elements.

TABLE II

| Curve - Element | Keeping Conditions |
| --- | --- |
| A - Example 3 | −18° C., 15% relative humidity |
| B - Example 3 | 25° C., 50% relative humidity |
| C - Control | −18° C., 15% relative humidity |
| D - Control | 25° C., 50% relative humidity |

The results show that the element prepared according to the present invention has significantly improved stability and keeping properties over the Control element prepared by wash coating the antisera into the spreading layer. This improved stability is seen by comparing the small difference between curves A and B versus the larger difference bwtween curves C and D. The difference between the two curves of each set of curves represents the loss in stability caused by keeping under high humidity conditions. The Control curves C and D show a large difference indicating that there was a considerable loss in stability in the Control element. The element of this invention exhibited 83.6% sens. ret. after 7 days compared to only about 21.1% sens. ret. for the Control element. $Rate_1$ was determined with a test sample containing about 22 I.U./λ CK-BB, and $Rate_2$ was determined with a test sample containing about 202 I.U./λ CK-BB.

EXAMPLE 4

Preparation and Use of an Analytical Element For Determination of CK-MB

An analytical element useful for the determination of CK-MB was prepared according to the procedure and format described in Example 2. It was tested for stability and keeping properties according to the procedure described in Example 3 except that CK-MB was applied to the element instead of CK-BB.

Similar elements were prepared by wash coating the antisera into an already coated and dried blush polymer spreading layer having the same composition except for the antisera. No ball milling was used to prepare the Control spreading layer. These elements are labeled Controls in this example.

Each type of element was kept under the conditions described in Example 2 and tested for stability or keeping properties by spotting them with test fluids having known amounts of CK-MB isoenzyme.

Figure 3:
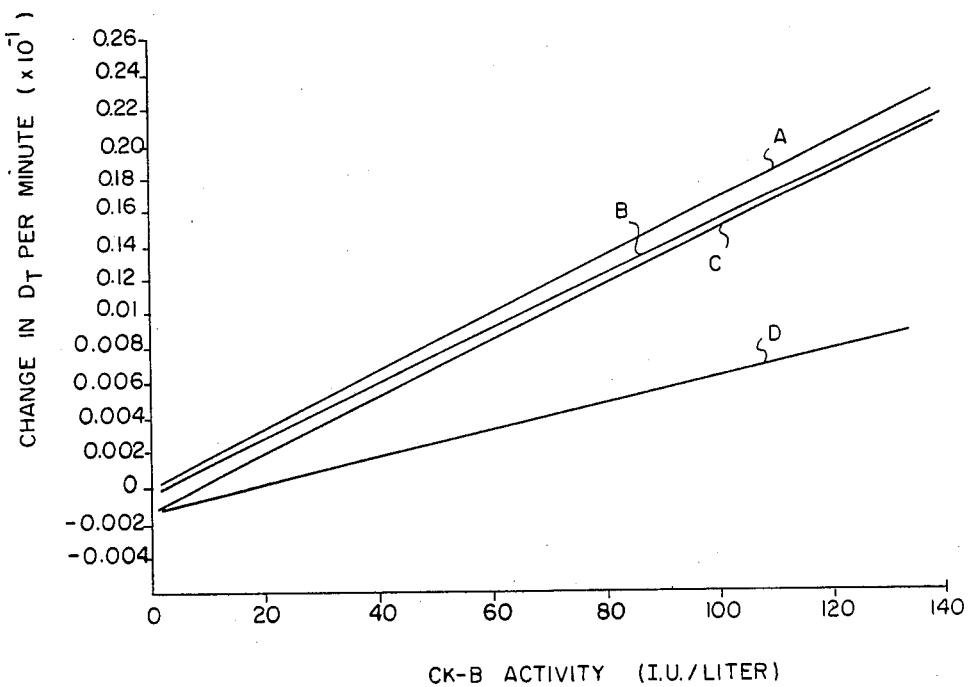
FIG. 3 is a graphical illustration of rate of change in transmission density ($D_T$) vs. CK-B activity for a number of compared elements as discussed in Example 4 below.

The rate of CK-MB activity was measured between 4 and 5 minutes after incubation at 37° C. using a modified conventional spectrophotometer at 670 nm and expressed as I.U. of CK-B per liter. FIG. 3 shows the results for each element. Table III below indicates the keeping conditions for the illustrated elements.

TABLE III

| Curve - Element | Keeping Conditions |
| --- | --- |
| A - Example 4 | −18° C., 15% relative humidity |
| B - Example 4 | 25° C., 50% relative humidity |
| C - Control | −18° C., 15% relative humidity |
| D - Control | 25° C., 50% relative humidity |

The results show that the element prepared according to the present invention has significantly improved stability and keeping properties over the Control element prepared by wash coating the antisera into the spreading layer. This improved stability is seen by comparing the small difference between curves A and B versus the large difference between curves C and D. The difference between the two curves of each set of curves represents the loss in stability caused by keeping under high humidity conditions. The Control curves C and D show a large difference indicating that there was a considerable loss in stability in the Control element. Further, the element of this invention exhibited 94.6% sens. ret. after 6 days compared to only 47.8% sens. ret. for the Control element. $Rate_2$ was determined with a test sample containing about 137 I.U./λ of CK-MB, and $Rate_1$ was determined with a test sample containing about 2 I.U./λ of CK-MB.

The invention has been described in detail with particular reference to preferred embodiments thereof, but it will be understood that variations and modifications can be effected within the spirit and scope of the invention.

We claim:

1. A method for preparing a blush polymer coating composition containing an active antibody or anti-antibody, said method comprising milling a dehydrated antibody or anti-antibody, a particulate material and a polymeric binder material in an organic solvent for a time sufficient to uniformly disperse said antibody or anti-antibody as particles less than about 5 μm in diameter in said binder material.

2. The method of claim 1 wherein said particulate material is an inorganic pigment.

3. The method of claim 2 wherein said pigment is titanium dioxide.

4. The method of claim 1 comprising milling antibodies for creatine kinase-MM.

5. The method of claim 1 wherein said binder material is cellulose acetate.

6. The method of claim 1 wherein said milling is carried out by sand milling, pebble milling or ball milling.

7. A method for preparing a blush polymer coating composition containing an active antibody or anti-antibody, said method comprising the steps of
dehydrating an antibody or anti-antibody, and
milling said dehydrated antibody or anti-antibody, a particulate material and a polymeric binder material in an organic solvent for a time sufficient to uniformly disperse said antibody or anti-antibody as particles less than about 5 μm in diameter within said binder material.

8. The method of claim 7 wherein said antibody or anti-antibody is lyophilized.

9. The method of claim 7 comprising milling antibodies for creatine kinase-MM.

10. The method of claim 7 wherein said particulate material is an inorganic pigment and said polymeric binder material is cellulose acetate.

11. The method of claim 9 wherein said coating composition comprises an activator for creatine kinase.

12. A method for preparing an analytical element comprising a porous blush polymer spreading layer containing an active antibody or anti-antibody, said method comprising applying the coating composition prepared according to claim 1 to a support.

13. The method of claim 12 wherein an intermediate layer is applied to said support prior to application of said blush polymer composition.

14. The method of claim 12 wherein said blush polymer composition is applied as the outermost layer of said element.

15. The method of claim 12 wherein said element is useful for the determination of creatine kinase-MB and comprises antibodies for creatine kinase-MM.

16. A method for preparing a multilayer analytical element for the determination of creatine kinase-MB, said method comprising
applying, in order to a support, a registration layer composition, a reagent layer composition containing creatine phosphate, and the coating composition prepared according to the method of claim 9.

17. The method of claim 16 wherein said blush polymer coating composition comprises cellulose acetate as said polymeric binder material, titanium dioxide as the particulate material, and a creatine kinase activator.

18. An analytical element for the determination of an analyte comprising a support having thereon a porous blush polymer spreading layer containing an active antibody or anti-antibody uniformly dispersed therein, whereby said element exhibits at least about 75% retained sensitivity for said analyte after being kept at 25° C. and 50% relative humidity for at least 6 days.

19. The element of claim 18 useful for the determination of creatine kinase-MB comprising, in order on said support, a registration layer, a reagent layer containing creatine phosphate and said spreading layer, and said element comprising antibodies for creatine kinase-MM.

20. A method for the determination of creatine kinase-MB in an aqueous liquid, said method comprising the steps of:
A. milling dehydrated antibodies for CK-MM, a particulate material and a polymeric binder in an organic solvent for a time sufficient to uniformly disperse said antibodies as particles less than about 5 μm in diameter in said binder material to form a blush polymer coating composition,
B. applying, in order to a support, a registration layer composition, a reagent layer composition containing creatine phosphate, and said blush polymer coating composition, and drying, to form an analytical element,
C. contacting said element with a sample of said aqueous liquid to produce a detectable change, and
D. determining said detectable change.

* * * * *